United States Patent [19]
Widding et al.

[11] Patent Number: 6,002,336
[45] Date of Patent: Dec. 14, 1999

[54] REACTION TIME MEASUREMENT SYSTEM

[75] Inventors: Erik Widding, Ithaca, N.Y.; Douglas DeAngelis, Worburn, Mass.; Andrew Barton, East Wittering, United Kingdom

[73] Assignee: Lynx System Developers, Inc., Woburn, Mass.

[21] Appl. No.: 08/982,952

[22] Filed: Dec. 2, 1997

[51] Int. Cl.[6] .................................................. G08B 23/00
[52] U.S. Cl. .................................. 340/573.1; 340/323 R; 340/539; 482/8; 482/19
[58] Field of Search ................................ 340/573.1, 665, 340/669, 323 R, 539; 482/8, 19; 200/61.45 R; 73/488, 379.01

[56] References Cited

U.S. PATENT DOCUMENTS

| | | | |
|---|---|---|---|
| 3,724,843 | 4/1973 | Fichter et al. | 340/323 R X |
| 3,731,298 | 5/1973 | Weidacher | 340/323 R X |
| 5,467,652 | 11/1995 | Richards | 73/379.01 |

OTHER PUBLICATIONS

"Calling time on jumping the gun," received Feb. 9, 1996.
Intersoft Electronics, "False start detection system," http://intersoft–electronics.com/sport/falsestart/falsestart.htm, Nov. 12, 1998.
Intersoft Electronics, "False Start," Brochure.
Seiko, "Starting System," Informational advertisement.
Sollicitation letter from Warren Gillete to Douglas De Angelis with product resume attached, Jun. 5, 1998.
Sollicitation letter from Allan Kirson to Paul Lambert, Feb. 24, 1998.

*Primary Examiner*—Thomas Mullen
*Attorney, Agent, or Firm*—Lahive & Cockfield, LLP

[57] ABSTRACT

The present invention provides a reaction time measurement system that includes a hard-wired or battery-powered accelerometer module attached to a starting block or platform to detect acceleration when a contestant moves. Although the block is grossly stationary, it undergoes slight movement and mechanical vibration, so the accelerometer produces an output signal. A filter or a processing unit in the module processes the output signal to define the reaction time or moment when the athlete starts to leave the block. Preferably the module removably attaches to the starting block by a rigid coupling, and its processor stores and annotates the accelerometer signal. A link or connector signals the reaction time, or the stored signal on request, to a central monitor at which false start detection determination are made and records created. The module may be used as an individual training device, in which a runner's readiness and take-off impulse are analysed as a reaction waveform, or his reaction time and starting speed recorded. For use in a track system, multiple separately addressed modules each annotate the accelerometer signal trace with one or more externally applied or synchronized timing marks.

16 Claims, 7 Drawing Sheets

REACTION TIME MEASUREMENT SYSTEM

BACKGROUND OF THE INVENTION

The present invention relates to apparatus and methods for evaluating an athlete's initial reaction or starting performance in a contest or practice event.

In a number of athletic competitions such as foot races, all contestants start at a fixed instant, and the performance of each is assessed by the order of crossing the finish line. Typically, in a track event, the runners each first assume a "ready" position on a starting block, and then push off when the start signal, usually an explosion from a starting gun, is given. In some aquatic events related arrangements exist wherein swimmers push off from a wall or release a grip on a support.

For longer track events, where each runner is confined to one lane and the paths curve, it is necessary to have the runners start at different stations which may be placed at staggered positions many meters apart, thus compensating for the incrementally increasing path lengths along the outside lanes. This assures that all runners arrive at a common finish line after running the full, fixed, distance. Because of the spaced-apart starting positions along the track, and because the speed of sound is only about three-hundred fifty meters per second, a delay of up to a tenth of a second is possible between the instant when the starting signal reaches the front starting block and when it reaches the back starting block. This delay can be minimized by appropriate placement of the starting gun to uniformize the distance, hence the sound signal transit time, to the various positions. In addition to this intrinsic spatial delay, each runner has a finite reaction time, typically about one to several tenths of a second, between hearing the sound and pushing off from the starting block. Moreover, the start of a race is a time of extreme nervous tension, and it is not uncommon for a runner to push off early before hearing the starting gun, or even before the gun has been fired.

In general, when such behavior is observed, a false start is called, and all runners must again line up and be prepared to take off. Several false starts may disqualify a runner. However, since the starting activity occurs when contestants are spread out over a number of different starting positions which may further be staggered from each other, and since a false start typically involves time intervals on the order of a small fraction of second, a false start may simply not be observed by the starter or judges, and may go undetected.

There do exist various automated systems which use specialized equipment for detecting false starts by accurately timing when each runner pushes off. Furthermore, some track association rules have codified the definition of a false start as one occurring in less than one hundred milliseconds after the starting signal. This interval corresponds both to the distance between the extreme front and rear starting positions along a standard track, and to a generally accepted minimal reaction time. It also corresponds roughly to the accuracy with which a human observer would be able to discern such a start. Judges may also exercise some discretion in calling a false start.

The general methodology used to detect a false start in the available automated detection systems is to employ a sensor which measures the force exerted by a runner on the starting block, and then to analyze the shape of the force curve to detect a moment which is considered to be the moment when the athlete has pushed off. That moment is then compared to the moment the starting signal was applied to determine whether the athlete's start was too early. The starting signal itself can be provided by an electronic trigger on the starting gun, or by a timing signal derived by detecting the starting shot with a microphone placed close to the gun. The runner's starting moment, determined by a curve analysis algorithm, is typically considered to be a point in time at which the force on the starting block passes a very high threshold, or a moment at which the force peaks. Automated start detection systems of this type generally require modifying the starting blocks, or providing specially configured starting blocks which, instead of transferring all force directly to the track surface, ride on a carriage and are arranged so that all or a portion of the force exerted by the athlete on the starting block is transferred to or through a force sensor, e.g., a strain gauge, which may for example be mounted between the block and the carriage.

One such commercially available system locates the force sensor in a position to detect force exerted in the backward direction, and it analyses the output to determine when the athlete exerts a threshhold force of about 250 Newtons, which is sufficiently high to be accepted as indicative that the athlete has reacted and is pushing off. Such a detection protocol, however, may introduce a certain level of inequality between runners, inasmuch as an athlete with a highly sprung set position normally exerting a force of 240 Newtons will trigger the sensor with a relatively small shift in tension or minor adjustment of his starting posture, whereas another individual who exerts only 100 Newtons in his ready position may be able to initiate more movement without exceeding the false start force threshhold or triggering an alarm. Furthermore, the commercial embodiment of this system requires a track organization to purchase a proprietary set of starting block assemblies.

Another similar system is based on specially modified starting blocks. This system also detects the change in force applied to the starting blocks, but uses a different algorithm to determine the athlete's moment of reaction.

Still another system in current use can be attached to various starting blocks by disassembling the starting block and attaching a special load bearing rear end to the block. In this system, the changes in force are converted to a voltage output which is digitized. As the runner pushes off, the maximum change in force achieved by the athlete is determined, and the moment of reaction, or actual starting time, is taken to be the instant when the curve reaches a threshold percentage, such as twenty per cent, of the maximum value.

Each of the foregoing approaches requires either a special proprietary starting block arrangement in which the block and force sensor are carried on a special carriage or otherwise formed of several components to house the strain detection structure, or else requires an invasive fitting to the preexisting starting block which involves disassembly of the block and attachment of special load bearing rear end to the block. Thus, to use one of the foregoing reaction-time measurement systems, one must either replace existing equipment or extensively customize it. These requirements impose a rather high capital requirement for updating a track system to reliably detect false starts, and conversely, they unduly limit an organization's ability to switch or replace starting block equipment once it has been acquired.

In general, the moment of starting is an important moment. The reaction time of one to several tenths of a second is a relatively large interval, which, for a short distance event, is comparable to the spread between a winning time and a time which does not even place. It is therefore important for an athlete to adopt a position which allows him to leave the block with the greatest possible speed, and to perfect his starting technique so that this is dependably achieved with the smallest reaction time and without false starts. However, practicing one's starting technique involves a cumbersome sequence of acts, and typically involves close observation by a coach. Thus, unlike many aspects of an athlete's performance, the starting reaction cannot be drilled in solitary practice. While an athlete's start may be objectively measured during an actual contest by the above-described systems, such equipment is itself too unwieldy for individual training and casual use by an athlete to improve his reaction time, and it also requires a monitor or operator.

It would therefore be desirable to provide a reaction time detection system which is simply applied to diverse existing starting blocks.

It would also be desirable to provide a reaction time detection system which sets up simply and dependably in a multiple-contestant system.

It would also be desirable to provide a reaction time detection system useful for individual training.

It would be further desirable to provide a reaction time detection system with enhanced warning, alarm, or signaling abilities.

It would further be desirable to provide a reaction time detection system which is automated to make false start determinations and interface with recording or display equipment of the host organization.

SUMMARY OF THE INVENTION

These and other desirable ends are achieved in a reaction time measurement system in accordance with the present invention wherein a starting block or platform, which may itself be conventional, is securely anchored in place, and an accelerometer is attached to the block so as to detect acceleration along one or more directions during the starting interval. The accelerometer produces an output signal indicative of instantaneous acceleration, and is preferably mounted in a robust block sensor module which is removably fitted to the starting block. Within the module a filter or processor receives the output signal and conditions or processes the signal to produce a reaction time indication or special detection signal when the athlete leaves the block. In a preferred embodiment, the block sensor module is conveniently attached to the starting block by a mechanically stiff or rigid coupling which is readily removable, such as a bayonet or dovetail coupling. The processor both processes and stores the accelerometer signal trace, and a link or connector communicates to a central viewing or monitoring station, to which the processor immediately sends the detected reaction time data with its lane or block address.

A speaker may be attached to or included in the block sensor module together with means for receiving a starting signal and/or other timing data, and a powered amplifier, oscillator or other means for actuating the speaker may be provided to produce a local sound so that the starting blocks at all positions can be actuated to emit an audible starting signal locally and simultaneously. For use in a track system, each block sensor has an electronic address which in different embodiments is advantageously initially selectively set to indicate its lane number, or is set by program control using an initialization procedure in a central monitor with which all blocks communicate. The modules preferably further include timing means in the processing units to produce a processed output indicating the interval between start signal and the detected reaction time on the recorded acceleration output signal trace for the period surrounding the start signal. The module responds to a query signal sent by the monitoring station and transmits that stored measurement data so that the actual acceleration curve may be visually inspected to confirm a false start determination, and may be printed out or otherwise stored for the record. The unit is preferably configured to process and report the athlete's detected reaction time or starting moment with a suitable time record, which may be based on the processor's local oscillator or clock, but includes as a reference time notation the starting gun signal and/or another initial instant which is common to the whole event such as the "set" signal, or a microphone-derived or electrically-switched start line signal.

For this purpose the module has one or more timing signal input lines or ports, which may be chained to the other block modules so that all modules communicate along a common bus or wire pair and possess a common time reference. However, preferably, rather than detection of false start directly at the block sensor, the module sends the detected reaction time to the monitoring station, referenced to an externally-provided time instant, and the monitor station receives the time reference and the reaction times from all the other block sensors, OR-ing the signals to produce a single signal which goes high at the instant the earliest reaction is detected. When this occurs earlier than a tenth of a second after the START signal, it is determined that a false start has occurred. Upon the occurrence of a false start, the monitor sends an audible alarm. It also queries the block sensors and receives their stored accelerometer signal traces so that the false start or starts of the athletes involved may be confirmed. Preferably, the monitor output also interfaces with other computerized athletic event timing or display equipment of conventional type to display the information that a false start has occurred, and the lane, name or number of the responsible athlete. The monitor performs various automated determinations. The monitor center and/or each module may include means for receiving a first signal indicating the starter's indication of "set", and preferably includes means for setting a mask time following the set signal in which relatively large perturbations or accelerations of the block are permitted, as the athletes adjust their stance, without triggering the false start signal. The monitor also receives a "start" signal, and sets a delay or false start detection interval following the start signal, in which a detected start will be considered too early. It may further be set to register a false start at any time after the mask interval and before the firing of the gun, although in general officials may wish to apply direct observation rather than automated timing detection to such very early movements.

In one embodiment, the block sensors are hard wired to the central monitor and communicate their reaction time determinations and acceleration waveform data thereto. In this embodiment they may receive power along the communications wires, and may both receive a common START signal and instantaneously communicate their initial reaction time determinations. In an alternative embodiment, the block sensors have their own battery power sources, and communicate by wireless transmission with the monitor unit. A preferred wireless link divides the broadcast time into two sets of interleaved communications subintervals. During the first subintervals the system transmits audio data to produce an isochronous sound output, used, for example to emit a local starting gun sound, while during the second subintervals the system transmits and receives digital time and signal data with message verification to create and reconstruct precision starting data records. Preferably the monitor unit includes further system data interface connections for uploading the reaction time of each position or optionally the fill waveforms from all the block sensors, to a further computer. The data records preferably include on each record an indication of the time of the set command and the firing of the starting gun. A user interface control center also permits entry of identification of the competition and race to be run, and prints out this information at the heading of a list of the runners' reaction times.

The invention further contemplates a single-module system embodiment adapted for personal training. In this embodiment a personal adaptor is configured to attach to the block sensor module to exchange information at a serial port, send queries and receive and display the recorded acceleration response curves so that the athlete or coach may see the nature of athlete's set and take-off reactions. The block sensor module is identical to those of the system block modules, although it need not possess addressing capabilities. Further the start timing input may instead simply receive a voice-actuated impulse, or may be replaced with a self-start system in which the user pushes a button, and the unit itself emits a start sound and timing pulse after a short but preferably randomized delay. In a preferred implementation and protocol for use of the individual training device, the module measures both the reaction acceleration of the starting block and the individual's initial speed. This is preferably done by arranging a photocell detector ahead of the runner, e.g. at ten meters, and providing the detector output to the accelerometer block module at the timing input port. The module processor then records both the reaction time and the detected crossing time, thus providing a direct measure of the overall quality or effective speed of the start achieved in that instance. In one embodiment, the personal training system may also locally process the accelerometer signal trace to detect the reaction time interval $\Delta T$ and trigger an audible alarm for each false start.

BRIEF DESCRIPTION OF THE DRAWINGS

These and other features of the invention will be understood from the description below taken together with figures illustrating elements of the invention and their configuration in a system, wherein.

DETAILED DESCRIPTION

Figure 2:
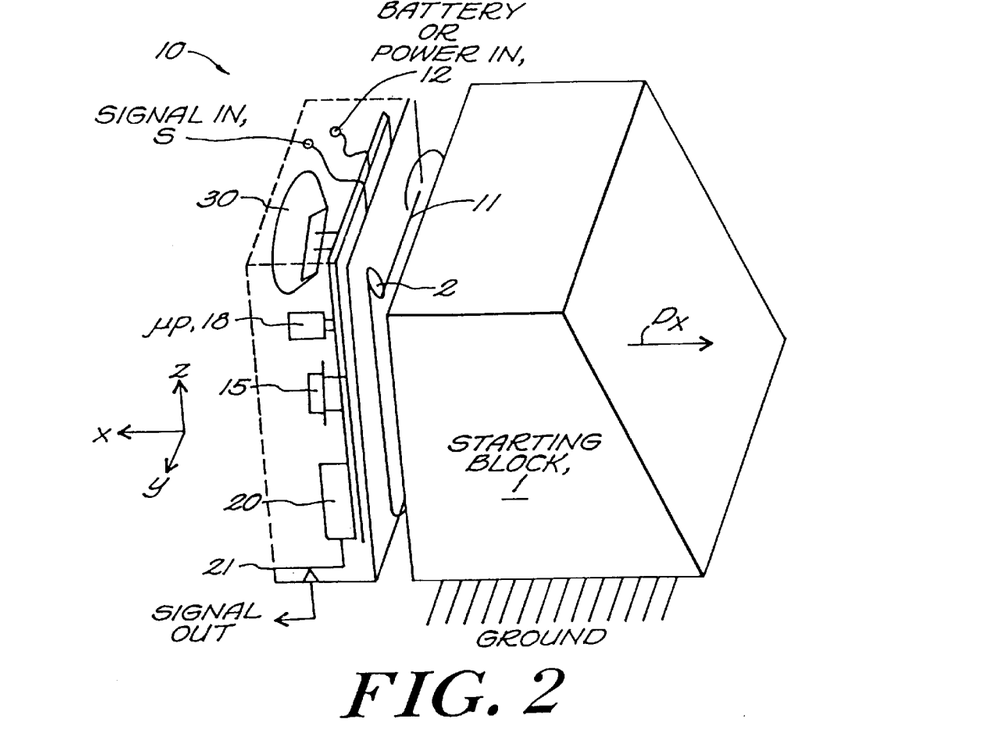
FIG. 2 shows a block sensor module of the present invention useful in the system of FIG. 1.

The invention will be best understood by reference to FIG. 2, which shows a reaction time block sensor or module 10 of the present invention. The module 10 attaches to a starting block or other sports platform 1 which, as shown, is anchored or rigidly connected to the ground, track or other fixed structure. The starting block 1 is therefore a stationary block, i.e., one that is substantially immobile. However applicant has found that despite being anchored and stationary in the grossly observable sense, the impulse of an athlete's starting reaction causes deflection and vibration of the block itself, and this gives rise to accelerations which are detectable in a manner which applicant has found to reliably reflect the reaction time and to define the starting moment of the athlete bearing against the block as the athlete pushes off. Thus, applicant realized that rather than requiring an elaborate mechanical carriage or structural assembly configured to receive force from the block, applicant could analyze the reaction and determine the start time by simply employing an accelerometer attached to the block.

Figure 2A:
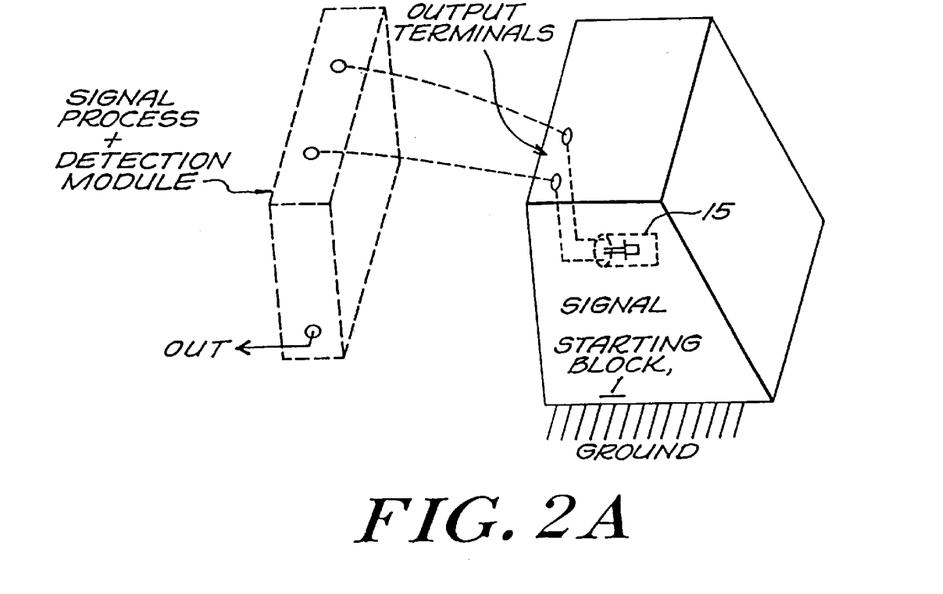
FIG. 2A shows another sensor module embodiment.

This is done in accordance with the method of the present invention by attaching a microchip accelerometer in or to the block, and detecting and processing its output. In one embodiment shown in FIG. 2A, an accelerometer chip is mounted directly inside the block, for example by drilling a hole in the block and cementing the chip 15 therein, providing a jack or terminal strip connector for attaching a separate processing circuit module. Preferably, however the invention is implemented as shown in FIG. 2, by providing a sensor module 10 which contains both an accelerometer unit 15 and certain processing circuitry, and which attaches to the block 1. The module 10 as shown is preferably connected by a catch or locking assembly 11 which engages a mating bracket 2 on the starting block to rigidly affix the sensor module 10 to the starting block 1. The catch and bracket arrangement may, for example, comprise a dovetail-like protrusion or a recess defined by catch 11 which slides together with a corresponding receiving shape of the bracket 2 to firmly but removably fasten the sensor module 10 on the starting block. The tapered wedge engagement (for a dovetail coupling) or other tight fit of two mating components assures a stiff coupling without looseness, so that any motion of the starting block 1 is directly and immediately transferred to the block sensor 10.

As shown, the block sensor 10 includes in its interior an accelerometer 15 which is a small, preferably solid state, sensing chip that responds to acceleration with a corresponding signal output, and also includes a processor 18 which receives an output signal along line 16 from the accelerometer, and an output port or communications link 20 which receives output data from the processor and applies it to an outside connection 21. The outside connection may be a hard-wired link or a wireless link. In some embodiments discussed further below, the sensor block 10 also includes a sound generating module such as a speaker 30, or a piezoelectric buzzer or tone generator. A source of electricity 12, which may be either a battery or a hard-wired electrical input line, provides power for the circuitry powering the processor 18 and any ancillary circuitry for digitizing, conditioning or processing the measurement signal produced by the accelerometer 15.

As further illustrated in FIG. 2, a signal input line S provides one or more external signals which are used as timing references. As discussed more fully below, these may include a set signal indicative that the contestants are to assume a position ready to start, and a start signal indicative that the firing gun has fired. This line may be a simple wired input, or a twisted pair serial data line so that the same port or line may also receive instruction or status query signals provided in digital format for causing the processor 18 to transfer either processed signals, or the raw data received by it along the line 16 from the accelerometer. In the event the communication module 20 is a wireless module, the system input signal line S may be part of the communications link rather than a wire connection. In that case a protocol discussed further below in connection with FIG. 6 handles both audio starting sounds and precision timing data messages which are dealt with appropriately by the processor.

As illustratively shown in FIG. 2, the starting block 1 is oriented for a track event with a runner pushing off in the direction indicated by the arrow denoted $D_X$. For purposes of the discussion below, this direction will be considered the x direction. As will be readily understood, the force of the runner pushing introduces an impulse in the rigidly coupled structure consisting of sensor block 10 and starting block 1 so that a slight perturbation or vibration, with its frequency, amplitude and damping characteristics largely determined by the rigidity of the materials of block 1 and the effectiveness of its anchoring to ground, will arise. This motion should have a component of acceleration in the x direction. Accordingly, as further indicated in the figure, the accelerometer 15 is mounted to have sensitivity to acceleration along the x direction, and, further, it is effectively rigidly coupled to the housing of the block 10 or to that portion of it most directly connected with the flange 11. However in a further aspect of the invention, applicant has found that the acceleration detected in the starting block is not necessarily predominantly directed along the x direction, but may for example be primarily along a direction transverse to the start direction $D_X$. While the physical causes of this apparent anomaly have not yet been fully explored, this is believed to result from several factors, including differences in foot positions and skew or shear-like starting impulses applied by different athletes, and structural features of the block geometry and anchoring assemblies that result in stimulation of certain modes or reflections of impulses in the mechanical system consisting of the mounting assembly, block, anchor and ground surface. The net effect is that some starts are characterized by a steep acceleration along the x axis, while others exhibit lesser x-axis movement and show their major disturbance along a transverse direction, such as the vertical axis. Accordingly, as discussed further below, the invention may also employ a two- or three-axis accelerometer to form the basic signal data. However, for purposes of the discussion herein, a single dimension of the accelerometer signal trace will be illustrated, it being understood that in cases where multi-axis sensing is carried out the processor will generally separately receive and process each channel, or combine them into a vector magnitude for performing its reaction time threshold acceleration determination.

The accelerometer 15 may take any of a number of forms, but is preferably implemented as a planar semiconductor device fabricated by microlithographic techniques having a displaceable or oscillating membrane, plank or beam with a small proof mass suspended on it, that changes frequency or position in response to acceleration exerted along a measurement direction, which may be perpendicular to the plane of the device. Thus, for instance, accelerometer 15 may be a flat microlithographic chip oriented substantially parallel to the connecting face of the sensor module 10. For purposes of discussion herein it will be simply assumed that the accelerometer 15 is provided with suitable conditioning circuitry so that it produces an output signal having a voltage which is proportional to the magnitude of acceleration, which as noted above, may be in the direction x, or have several output voltages representing acceleration along several axes.

Figure 5:
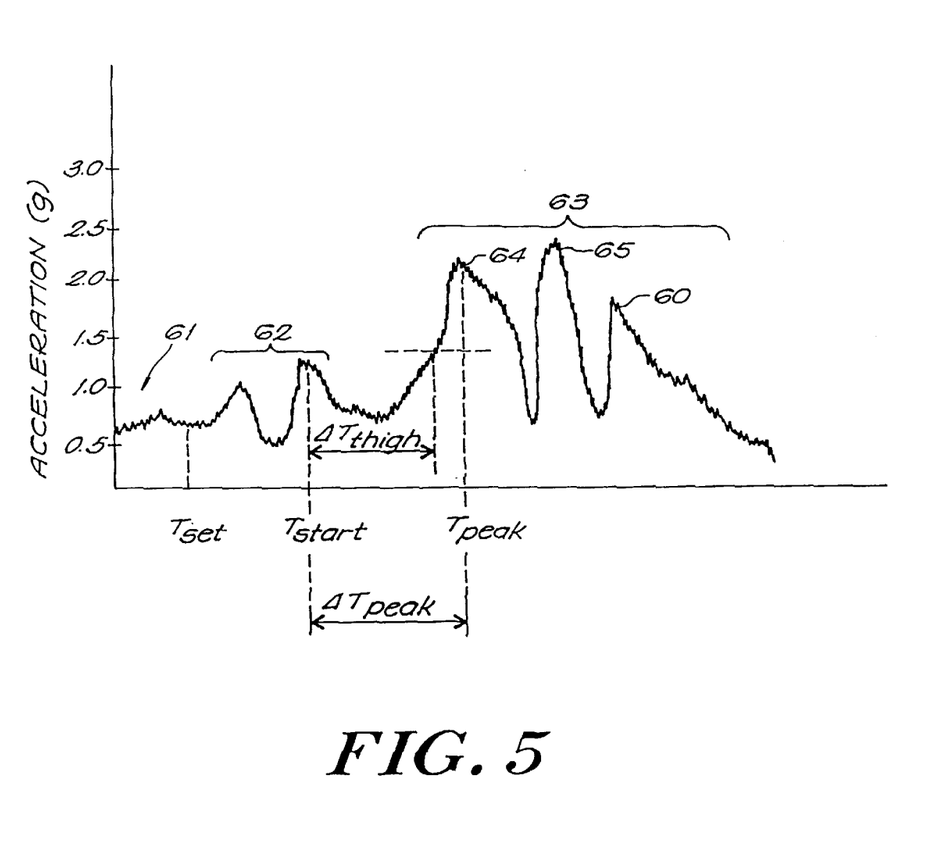
FIG. 5 shows a representative stored signal trace.

FIG. 5 shows a typical such signal for an accelerometer 15 coupled to a starting block in use. The vertical scale is calibrated 0 to 3 g acceleration, while the time scale on the horizontal axis is arbitrary. As shown, the output signal is sampled at frequent intervals, preferably several thousand times per second, and has a jitter indicative of the noise level of various system components, including circuit noise as well as the vibrational or structural noise of the block itself. The signal exhibits several distinct patterns of amplitude fluctuation, including the macroscopic noise level or jitter between adjacent measurement points, a larger variation occurring at much lower frequency corresponding to low level physical oscillations and applied forces, as shown in region 62, and a region of much greater acceleration denoted 63 in the Figure. The wave form exhibited in region 62 is characterized by attaining a significant but not extreme magnitude and having a relatively stable overall appearance in that it may have discrete disturbances of low to moderate amplitude that may recur several times, or may simply return to the background signal level similar to that shown in the jitter region 61. In the region 63, on the other hand, a significant increase in acceleration occurs, rising over a threshold level illustratively 1g and coming to a peak 64 which then falls off, indicating that the applied force has caused an initial sharp structural or vibratory impulse. Thereafter, one or more smaller peaks 65, 66 may (but need not necessarily) occur, with generally decreasing amplitude due to residual oscillation of the starting block assembly. The presence or shape of such post-peak dropoff, and the occurrence of additional peaks may depend substantially on the materials of the starting block and track surface, as well as the nature of the anchoring to the ground and other factors which effect structural damping of the block assembly and stiffness of the connection between that structure and the sensing accelerometer.

As further shown in the accelerometer trace of FIG. 5, several additional timing points are marked on the horizontal time axis in addition to the time of the acceleration peak 64, denoted $T_{peak}$. These include a first time annotation $T_{set}$ which occurs in the region 61 of typical background accelerometer signal level when the starter gives the "set" signal for runners to assume their starting positions. This is an externally-provided time impulse, which provides a reference or zero point for the time scale of the module 10 so its data may be referenced to all other modules connected in the system. Shortly thereafter, the moderate level disturbances of region 62 start as the runners position their feet in readiness against the block and commence to build up force against the starter block 1. Thereafter, a second time instant $T_{start}$ is shown, illustratively occurring during one of the minor disturbance peaks of region 62. These moderate acceleration levels indicate that the runner was still adjusting his stance but had not yet reacted at the time of the signal. This $T_{start}$ is also a timing signal which is externally applied to the sensor module from the starting gun, and it constitutes another objective time reference to assure that the signal traces generated by all the modules can be compared to each other on a common time scale. As further shown in this particular signal trace, during a brief time after the start signal $T_{start}$ the accelerometer output level has again dropped below its intermediate level indicating that the runner has settled in readiness and has not yet reacted to the starting gun. Thereafter, however, acceleration starts to climb, crossing a threshold, illustratively at about 1.5 g, and rising to a sharp peak before falling into a period of high amplitude oscillation.

The foregoing curve is illustrative only, and is intended both to show the time annotations provided in the stored processed signal trace, and representative signal outputs associated with various states of relaxation or disturbance as the runner positions himself and reacts to the starting signal.

In practice, the unannotated accelerometer output signal is digitized and fed to the processor which receives the external timing signals, and processes the output trace of the accelerometer, storing it together with one or more of these time signals as an annotated signal trace.

Figure 3:
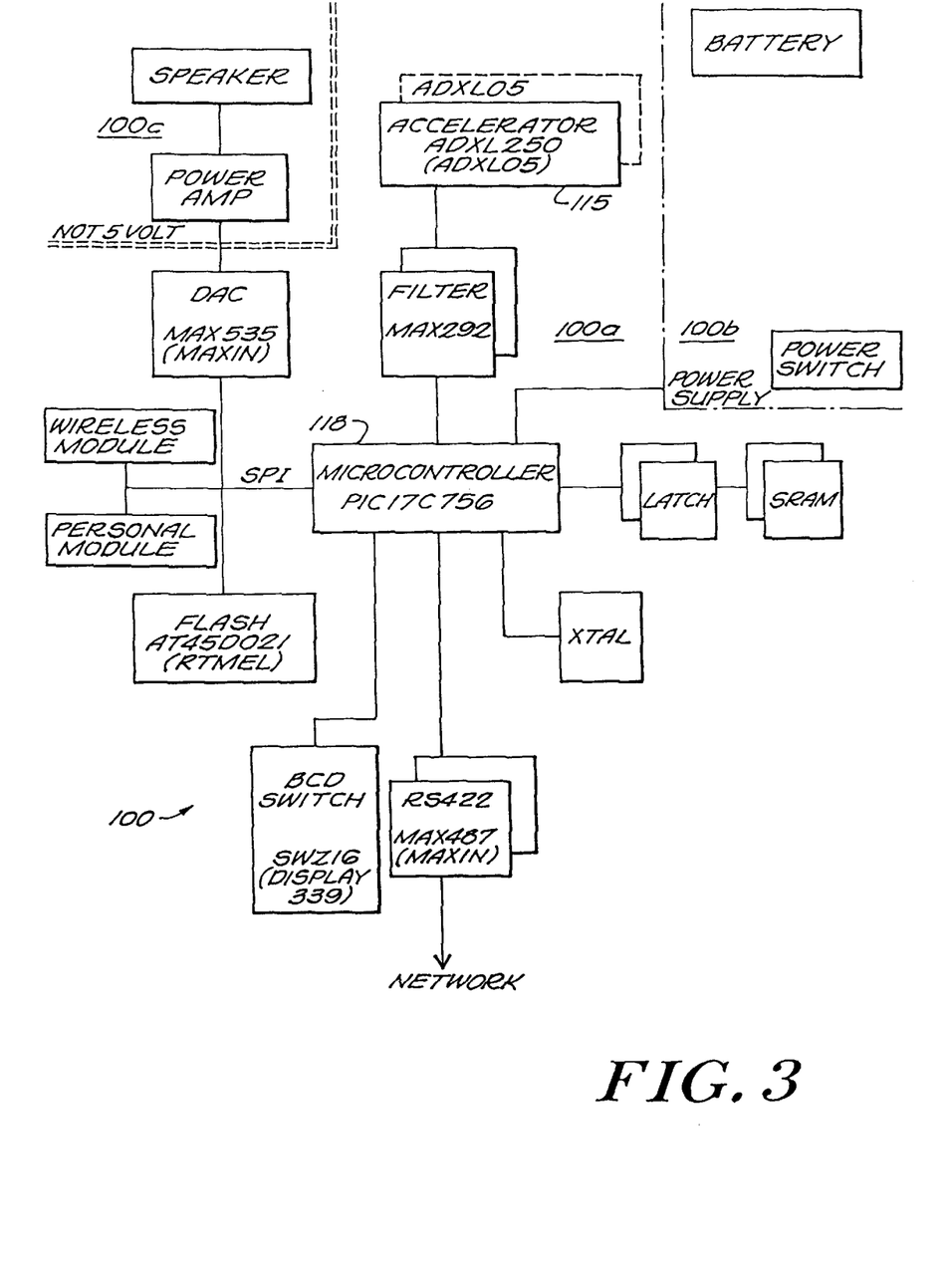
FIG. 3 show a more detailed schematic of a prototype sensor module like that of FIG. 2.

FIG. 3 is a more detailed schematic of a prototype module 100 of the present invention. As shown, module 100 of this embodiment includes a primary functional group 100a with the accelerometer 115 and a microcontroller/processor 118, and further includes a secondary functional group 100b constituting a power supply, and a third functional group 100c constituting a sound source. By "functional group" is meant simply a component or group of components which implement the described function. Thus, the power supply functional group is implemented in one embodiment with a battery and a power switch, either as a separate power supply box that plugs onto the sensor module, or as components mounted in the module, i.e., a switch and a removable battery. This group may take any number of common forms or variations, such as including a rechargeable battery and suitable charging circuitry, indicator LEDs and the like. Functional group 100b could alternatively simply consist of a power input port which provides a connection along which the circuitry receives power from an external source, for example as a bias potential applied across data wires used for external communications or data transfer. Similarly, the audio signal functional group 100c, which is shown as including a power amplifier and a speaker or other sound transducer, may be integral with the accelerometer portion 100a, for example as a potted unit, or may be a plug-in assembly provided as an option to augment the basic sensor module.

In one such embodiment, the reaction time unit is used in a multi-unit system for athletic contests, and each module has an external input XLR1 (FIG. 4) at which it receives a "start" time signal message. In this embodiment the microcontroller controls the sound source 100c to provide a local "start" sound, e.g., a loud tone burst or an explosive sound comparable to the sound of a starting gun. In another embodiment discussed further below, the module is to be used alone, that is, as a single unit, by an athlete as a personal training device to practice his set and starting technique. In this case, the audio unit and controller may be set up to emit a "set" sound, followed by a "start" sound at a short but preferably randomized later interval, while recording the accelerometer output. The unit thus runs a "practice start", or as described more fully below, a series of practice starts which preferably also signal and record one or more further aspects of the athlete's performance, such as his starting speed, in order to more effectively evaluate the combined effects of reaction time and starting efficiency or power.

Figure 4:
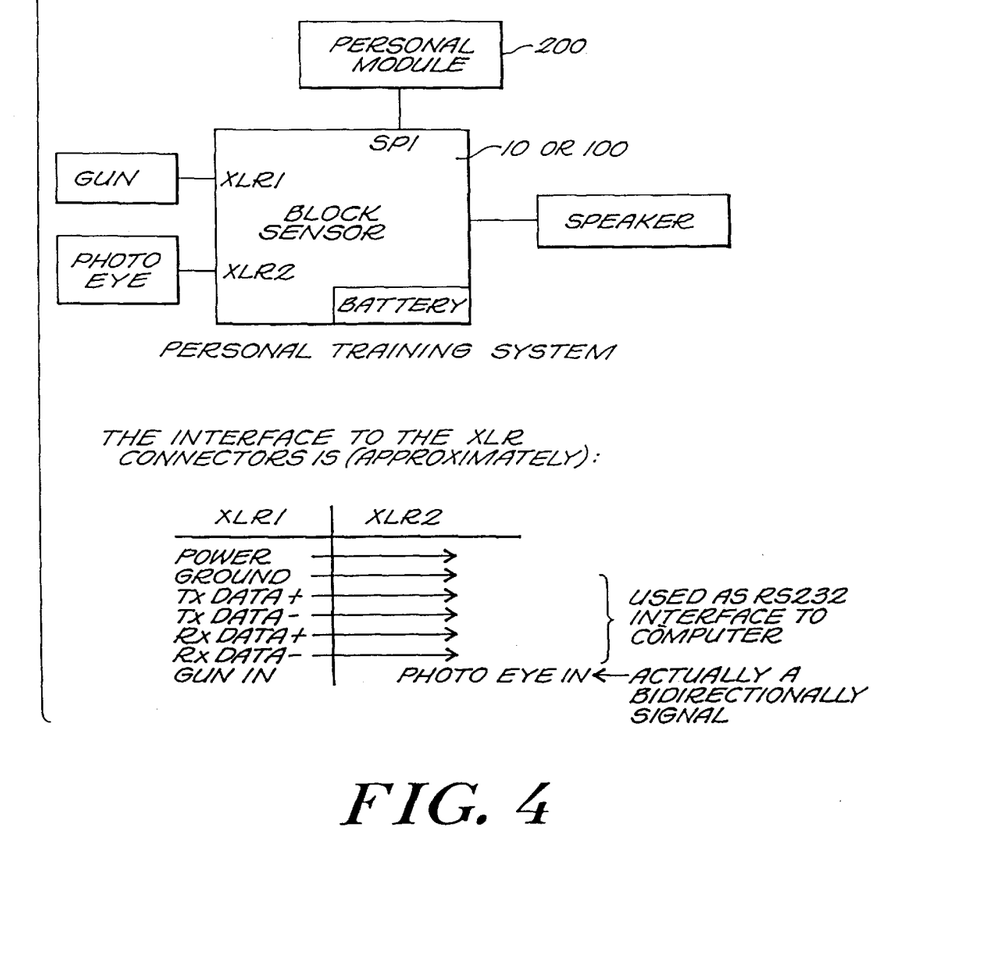
FIG. 4 illustrates features of a personal training system with the sensor module of the invention.

Such operation is achieved with a fourth functional unit 200, shown in FIG. 4. Unit 200 augments a single sensor module to provide an individual system for personal training as just described. As noted above, the basic sensor module 10 or 100 employed in a multi-unit system digitizes and stores the accelerometer signal trace during the time interval around the start signal, and annotates that trace with at least one common external time signal, preferably the start signal. The unit 200 is adapted to attach to a communication port SP1 of the sensor module, illustratively a serial data port, and allow the sensor block to function as a stand-alone unit for individual training. The personal adaptor unit 200 may actuate a starting sequence in the sensor block, and it thereafter receives stored information to display data for immediate feedback to the athlete. Preferably the sensor module receives a photo eye signal, illustratively at an input port XLR2, from a crossing line photocell which is positioned near the block, for example at ten meters from the starting position, and the time of this signal is also incorporated into the accelerometer trace stored by the module. In a basic embodiment of such a system attached to a crossing detector, the personal adaptor unit 200 displays the time from the start signal to the instant the athlete reaches the ten meter mark, thus giving an objective measure of the overall effectiveness—the average starting velocity including any reaction delay—associated with each start. This may be displayed with a simple alphanumeric display interfaced by basic circuit elements in the unit 200.

Figure 4A:
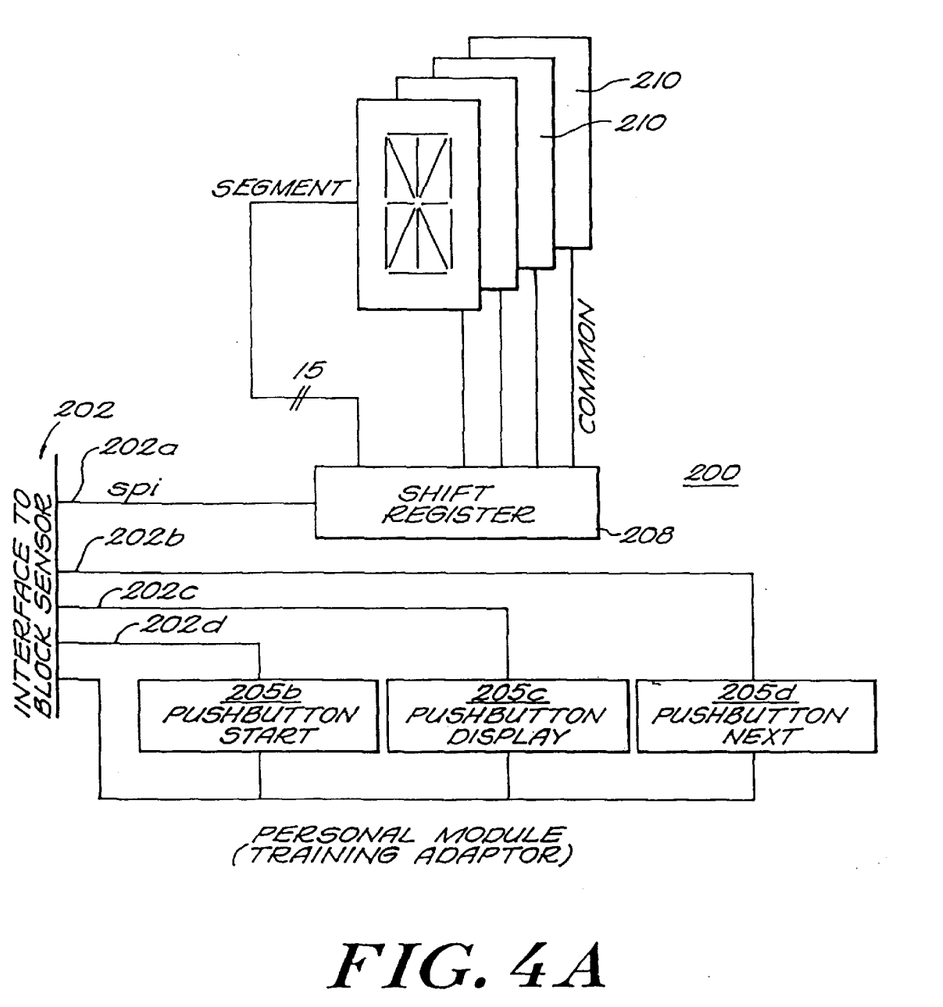
FIG. 4A illustrates elements of a personal module for adapting the sensor module in the system of FIG. 4.

FIG. 4A shows relevant components of the adaptor 200. As shown, a plug and/or wire terminal strip connector 202 connects to a serial data line 202a and to a plurality of individual voltage level signal lines 202b, 202c, 202d. . . Each of the signal level lines is connected to a corresponding button switch 205b, 205c or 205d, and the athlete presses the appropriate button to actuate processing operations which have been previously programmed into the sensor block 10. By way of example, button 205b may actuate a simulated start program, in which the module waits a few seconds, then emits a special "set" tone from the speaker to warm the athlete to get ready, and then after several more seconds causes the speaker to emit an explosive burst sound as a starting signal. All the while, as noted above, the module 10 or 100 is recording the accelerometer signal trace, and the times of the simulated start signals are incorporated in that trace data, just as for externally provided "set" and "start" signals in the multi-unit event system configuration described above. Such storage and annotation is implemented in a straightforward way. For example the accelerometer signal may be digitized and sent to a recirculating buffer, and the current several seconds of the signal trace from the accelerometer output data is stored each time a START signal is received.

Returning to a description of FIG. 4A, the second pushbutton 205c may take the place of the central monitor query message of the full race multi-module system, and is pushed by the athlete after he has performed one or more practice starts to cause the sensor module to send its stored signal trace or starting time interval data to a display 210 in the personal adaptor 200. The third button can implement a NEXT message when the microcontroller is configured to store several sets of start data, or a RESET message. When one of the buttons calls for time data from the sensor module 100, the received data is sent to a shift register 208 and applied to a set of four fifteen segment alphanumeric display elements $210_i$. The user thus reads his ten-meter time directly on the face of unit 200. Optionally, the microprocessor of the block sensor 100 may be programmed to determine the actual reaction time from the accelerometer data, using a thresholding, peak detection or other automated numerical analysis or signal evaluation test. In that case, the data sent to the adaptor unit 200 may include the START time, the detected reaction time and the ten-meter photocell crossing time, or may include the reaction time followed by a processed or derived data measure, such as the starting velocity, either averaged from the START signal, or corrected for the reaction time delay. Preferably, the microcontroller of module 100 is programmed in various different embodiments to implement the data outputs for personal training. Presently, the preferred system simply outputs the time interval between the start burst and the ten-meter crossing time detected by the photocell. This allows the athlete to practice alone and optimize his starts, without requiring a coach or other personnel to either view his technique or provide signals to the equipment or cues to the athlete. As noted above this start burst is part of a sequence of programmed timing signals specifically generated for the training system, and this may be readily implemented by an analog trigger and switch elements, or by a set of programmed interval counters with a pseudo-random dither added to assure that the start signal does not occur at a predictable instant. In further embodiments, the processor of the sensor module may perform the basic analysis of the accelerometer signal trace described above to determine the reaction time or starting moment, and may indicate that reaction time as a digital output signal to the adaptor 200. In that case, the athlete may inspect the interplay between his time off the block and the resulting initial speed. The module may also actuate a false start alarm at the speaker when it is used in the personal training mode and a premature start is detected. In still another embodiment the personal adaptor module 200 may include a graphic display, instead of or in addition to the alphanumeric display, to show the complete accelerometer trace produced and stored by the sensor module 100. This information may provide a useful characterization of the early phase of an athlete's starting technique, and may help to pinpoint postural inefficiencies of his start position. Thus, the outputs of the sensor module not only provide an immediate measure of reaction time for training purposes, but constitute an analytical tool for studying and improving the relationship between reaction time and effective starting technique.

Figure 1:
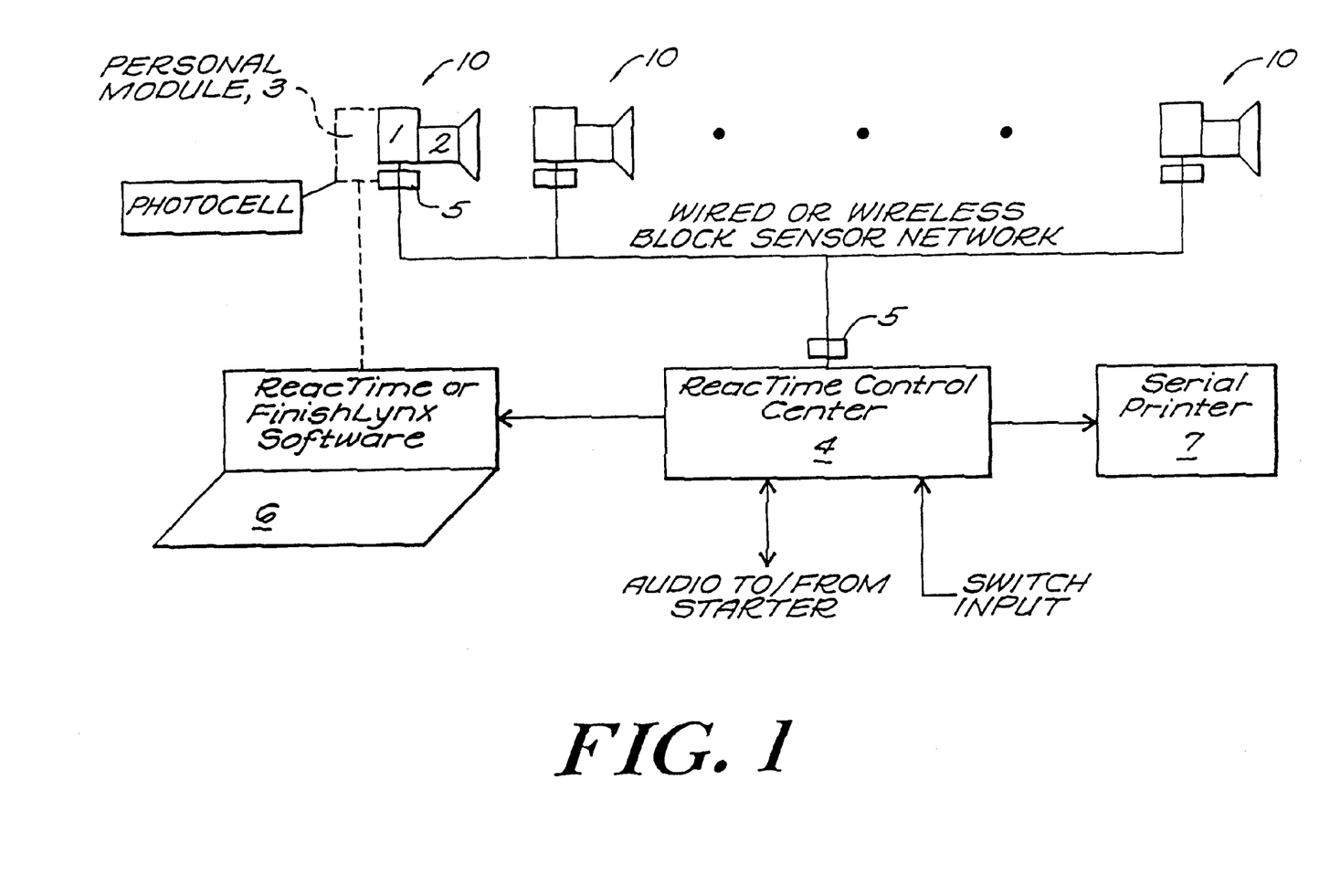
FIG. 1 is a block diagram of a reaction time detection system of the present invention.

Returning now to a description of the full starting line system with multiple sensor block modules (FIGS. 1 and 3), when implemented as a hard-wired system, the sensor modules preferably connect in a loop and each continually processes its accelerometer data and sends a signal as soon as it detects a reaction indicating the athlete's start. The central monitor receives the START signal as well as these reaction time signals from all the modules 10, and determines that a false start has occurred if such a reaction signal is received from any module too soon after the START signal. Optionally, the central monitor 40 and/or each sensor module 10 also receives a first signal indicating the starters indication of "set", and responds to this signal by instituting a mask time following the set signal in which relatively large perturbations or accelerations are permitted (at the modules 10) or reaction time signals are ignored (at the monitor 40), as the athletes adjust their stance, without triggering the reaction time output of the modules or the false start output signal of the central monitor. In general, once the mask interval has elapsed, the monitor receives the incoming signals from all modules, ORs them to produce a signal the presence of which indicates that someone has moved, and actuates the false start alarm if this signal occurs before one hundred milliseconds have elapsed following the starting gun signal. Optionally, when the judging authority elects to employ automated rather than visual detection of premature actions occurring even before the starting gun has fired, the monitor may be "armed" to trigger even before the starting gun moment, for example by a push button which actuates the logical OR input alarm circuit, or which applies the set signal to the START signal input. At the central monitor station, the microprocessor is configured so that once a false start has been detected, it requests and then stores the full accelerometer record and block address or other identifier from the responding sensor modules. A user interface also permits entry of identification of the competition and race to be run, and this information is printed out at the heading of a list of the runners' reaction times. Thus the monitor serves the function of comparing and performing determinations for the outputs of the several block sensors, and of generating records, creating alarms, and providing a digital data interface to such display or imaging systems as may be installed at the sports facility.

The implementation of these features is a straightforward matter of programming, and the use of a wire data line or a more complex ring bus protocol readily allows the false start determination to be made and an alarm effectively sounded within a small fraction of a second. It also allows a common time standard to be sent to all units. In other respects, the monitor system is configured to rely on a small number of signals which contain essential time or address/lane information. Thus, by communicating at a data rate of fifty to several hundred kilobits per second, the system readily detects false starts with imperceptible delay, and acquires and displays the relevant traces so they may be immediately inspected. In a further embodiment of the invention, this data is interfaced with or combined with other athletic measurement or display data from other systems. For example, the module addresses can be indexed to or set identical to the lane numbers, and these may be indexed to the contestants' names, so that that the "false start" message is converted, updated with the identity of the athlete, and sent to the facility's display system to display a message identifying the responsible contestant. The data may further be interfaced to the system to display the relative starting times of the contestants, thus serving as an initial performance measure of interest to the audience.

When the modules are hard-wired in a loop with the central monitor, each may have an input port, and an output port which connects to the next module 10. The data and messages may circulate in a well known communication protocol by receiving, inspecting the address, resending and/or augmenting each communication so that each message reaches its intended recipient in a short time. However in a preferred wired embodiment, a much simpler and direct protocol is used. Since the initial determination only requires that the central monitor recognize that some module has sent out a reaction time signal, this data may be sent in parallel by all modules; the line is simply set HIGH or LOW to indicate a detected reaction. Further, with such a hard wired communication path, the central monitor is preferably programmed to automatically establish the address and identify the lane number of each module. This is effected by a simple initialization procedure in which the first module is polled, caused to wiggle its output line which connects to the next module, and the module which detects a wiggled signal on its input line then sends out its address. The process is continued to determine the addresses of all sensor modules in the order of their occurrence along the wire. Thereafter, when the central monitor operates to request accelerometer signal traces and timing data, the communications are effected as formatted messages, in which module address, framing bits, and data bits are transmitted so that the monitor can assemble the fall record from each module.

It will be apparent that the only critical requirement for assuring that the accelerometer traces are highly accurate is that there be a common time reference containing the START signal. Since this signal is presented simultaneously to all modules along the wire communications bus, that condition is fulfilled. Each microprocessor has a local clock or crystal oscillator of defined frequency which controls the reading and storing of processed accelerometer signals, and these clocks are sufficiently accurate that any deviations during the several seconds of accelerometer signal trace are well under a millisecond. For providing the local START sound to the speakers in each module, the preferred system preferably sends the actual audio or digital audio signal along the common wire bus to all modules. The powered speaker units then amplify and emit the sound locally all at the same time.

Preferably, the entire system of block sensor modules and central monitor is configured with wireless communications links between the units. For much of the data involved, conventional packet radio messaging protocols are sufficient. In one presently preferred embodiment, however, the radio communications are effected in a transmitter/receiver system that implements both guaranteed and nonguaranteed messaging on a single transmission channel or hardware unit. The unit achieves simultaneous data transmission/reconstruction for one class of data, and highly accurate data transmission/reconstruction for another class of data. This is done as shown in FIG. 6.

Figure 6:
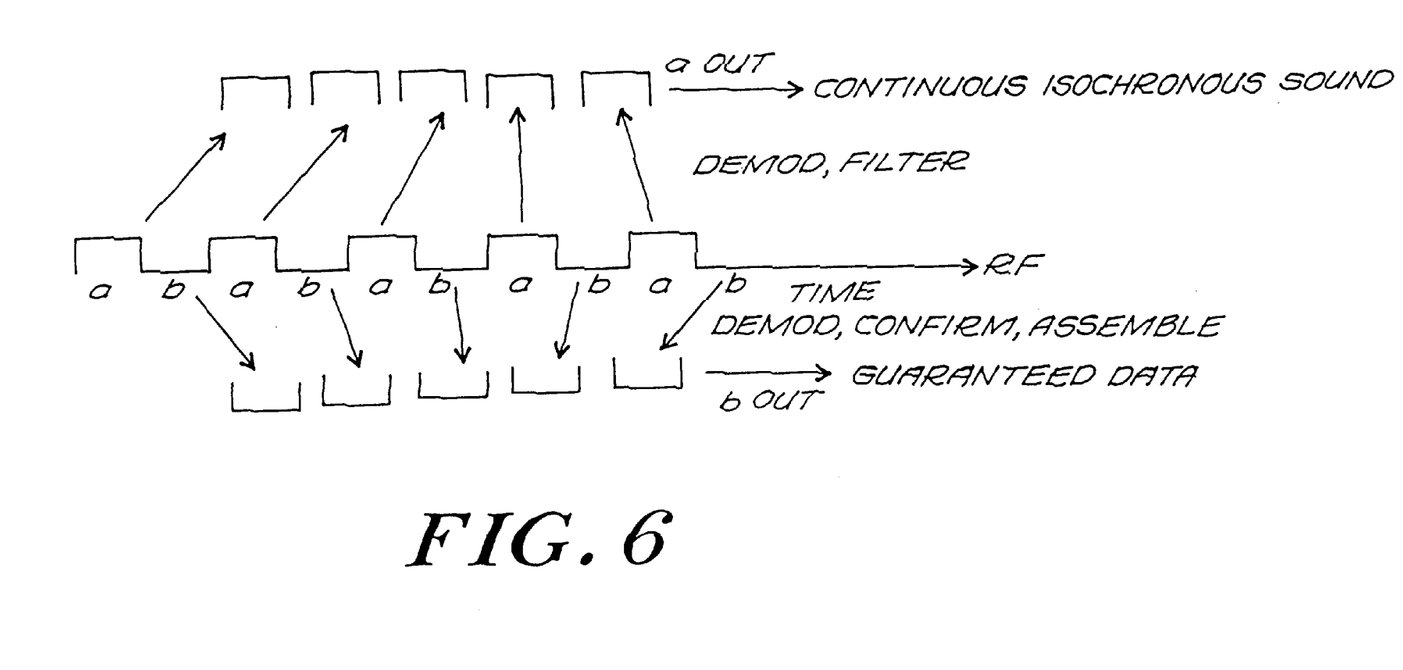
FIG. 6 illustrates a communications protocol of a preferred wireless system in accordance with the present invention.

As illustrated in FIG. 6, the RF communication is sent as a time division message sequence in which first intervals "a" alternate with second intervals "b" in a regular fashion. During each interval a,b digitally encoded data is transmitted, with the receiving units staying synchronized with the transmissions in a well known way by use of framing or timing bits, synchonous demodulation, and time synchronization or phase-locking feedback loops or other suitable techniques.

By way of example, the intervals a,b may each have a fixed duration, typically between about ten and a thousand times the period of the basic RF carrier frequency. In accordance with this aspect of the present invention, the intervals a are all assembled into one consecutive data stream at the receiver output, while the intervals b are segregated into a second data stream. Furthermore, the first data stream is employed to carry digitized audio signals of the starter gun or burst. This results in a data stream a out which is essentially continuous, and is received simultaneously and identically by all block sensor modules. While dropouts may occur in each reception, the individual intervals a are so short that the failure of individual intervals to be properly received or demodulated will not affect the overall sound which extends for several milliseconds over many transmission intervals. The a messages are therefore simply sent, without acknowledgement protocols, or optionally without error coding, and the received a messages are D/A converted, passed through an analog filter, amplified and emitted as the starting signal from the block module speakers. The filter may even be omitted, as the use of analog electronic or speaker elements sufficiently smooths the received sound.

The b message stream on the other hand is used for communications relating to timing, signal data, module addresses and the like, and the b messages may be, and preferably are generally coded with an error detection or correction code, which is checked to assure message integrity; the receiving unit then acknowledges receiving the b message, and in default of a timely acknowledgement the message is retransmitted, as is commonly done for time division digital transmissions and packet radio communications. This allows the receiver to accurately acquire relatively large blocks of data such as the accelerometer signal traces, and to verify or assure accuracy of the module addresses. These b messages, in addition to carrying the digital signal trace records and the like, may be used to provide time synchronization signals to the modules, allowing each module to periodically update its local time so that the stored data records of each module share a time scale which is accurate to well under one millisecond. However, in a presently preferred implementation, the time standard signals, although broadcast as b messages, are not subject to a message acknowledgement protocol. Instead, they are broadcast many times per second, and when received the receiving module simply checks the error code, passes the data to its time synchronization update handler if accurate, and discards the data if it is inaccurate. Correspondingly, at the transmitter end, time synchronization data messages are handled as though automatically acknowledged and no checking or retransmission are performed. Thus, while the b data includes guaranteed messages, it need not consist entirely of verified transmissions, and the communications flexibly accommodate transmission of different messages to optimize speed, accuracy or synchronicity.Thus the wireless communication between monitor and block modules includes a continuous, isochronous data channel of non-guaranteed data, and a guaranteed data channel which, while not instantaneous, can provide message integrity and assure that system time is accurately maintained in all receiving locations.

In the wireless transmission embodiment the modules each have their own power source, and the radio communication protocol assures that all messages are heard within a short time interval. In this embodiment, the actual lane location of each module is preferably established by extrinsic means—either programmed in and marked on the module housing, or manually ascertained each time after being set up. In each case, while the microprocessors of the sensor modules each have a system clock, it is preferable that the time reference be broadcast to all modules and stored by them such that when they later transmit data the time scale will either have a common point of reference, or will have been internally corrected to a desired degree of accuracy.

This completes a description of a basic embodiment of the invention and illustrative variations thereof applied to a starting block reaction time measurement system. The invention will be seen to be conveniently adaptable to diverse existing models of training and sports equipment, and be useful for a range of detection, measurement, timing and display systems to which it is readily fitted or interfaced by virtue of its simple physical construction and its electronic data annotation and output signals. The invention being thus disclosed and described, variations and modifications will occur to those skilled in the art, and all such variations and modifications are considered to be within the scope of the invention as set forth and defined by the claims appended hereto.

What is claimed is:

1. A reaction time detection system for determining an athlete's starting reaction, such detection system comprising
   a detection unit attachable to a fixed block or platform against which an athlete bears in a pre-start position, wherein the detection unit includes an accelerometer mounted in said unit to move with said fixed block or platform and produce an accelerometer signal indicative of motion thereof, and
   a processor for processing said accelerometer signal to detect the athlete's starting reaction time.

2. A reaction time detection system according to claim 1, wherein said processor is included in said attachable detection unit, and further including means for storing the signal from the accelerometer over a time interval, together with an initial time signal, the initial time signal being a common time signal provided to plural detection units so that the starting reactions of multiple contestants are compared in time.

3. A reaction time detection system according to claim 2, wherein the accelerometer has a measurement axis aligned with a starting direction.

4. A reaction time detection system according to claim 3, wherein the accelerometer has plural measurement axes, and one of said axes is aligned transverse to a starting direction.

5. A reaction time detection system according to claim 1, wherein the detection unit includes a sound emitter configured to emit a start sound audible to the athlete whereby contestants simultaneously hear a starting signal.

6. A reaction time detection system according to claim 5, wherein the detection unit compares the identified starting reaction to common received time to identify a false start, and wherein said sound emitter emits an alarm sound to signal when a false start is identified.

7. A reaction time detection system according to claim 1, wherein the detection unit determines a threshold of said acceleration signal to detect said reaction time.

8. A reaction time detection system according to claim 1, wherein the detection unit filters the acceleration signal to remove noise.

9. A reaction time detection system according to claim 1, wherein the detection unit determines a starting time interval.

10. A reaction time detection system according to claim 9, further including personal means attachable to said detection unit for viewing the detected time interval.

11. A reaction time detection system according to claim 10, wherein the detection unit further includes means for receiving a line-crossing signal, and said processor determines said time interval to the time of line crossing whereby the athlete may evaluate starting effectiveness.

12. A reaction time detection system according to claim 10, wherein said processor stores and said personal means displays multiple sets of reaction time and line-crossing data for the athlete to evaluate starting effectiveness.

13. A reaction time detection system according to claim 10, wherein the personal means further includes means for detecting and signaling a false start.

14. A reaction time detection system according to claim 1, further comprising a central monitor in communication with said detection system and being operable to receive said reaction time determination produced by plural detection units, and detect a false start, said central monitor producing an alarm signal upon detection of a false start.

15. A reaction time detection system according to claim 14, wherein said central monitor communicates by wireless communication with said detection unit.

16. A reaction time detection system according to claim 15, wherein said wireless communication includes first and second sets of communication intervals, said intervals being regularly alternating to effect a first data set of isochronous sound received by all detection units simultaneously and a second data set of time data reconstructed from guaranteed communication messages, said first and second sets being communicated via a common receiving channel.

* * * * *

UNITED STATES PATENT AND TRADEMARK OFFICE
CERTIFICATE OF CORRECTION

PATENT NO. : 6,002,336
DATED : December 14, 1999
INVENTOR(S) : Erik Widding, et al.

It is certified that error appears in the above-identified patent and that said Letters Patent is hereby corrected as shown below:

On the title page, after:

--[75] Inventors: Erik Widding, Ithaca, N.Y.; Douglas DeAngelis,-- replace "Worburn" with --Woburn--

Signed and Sealed this

Eleventh Day of July, 2000

*Attest:*

Q. TODD DICKINSON

*Attesting Officer*     *Director of Patents and Trademarks*